United States Patent [19]

Carter

[11] Patent Number: 4,538,018
[45] Date of Patent: Aug. 27, 1985

[54] SURFACE CONDITIONING IN OLEFIN DIMERIZATION REACTORS

[75] Inventor: Cecil O. Carter, Wann, Okla.

[73] Assignee: Phillips Petroleum Company, Bartlesville, Okla.

[21] Appl. No.: 560,788

[22] Filed: Dec. 13, 1983

[51] Int. Cl.³ .............................................. C07C 2/24
[52] U.S. Cl. ..................... 585/512; 585/510; 585/950; 208/48 R
[58] Field of Search ....................... 585/950, 510, 512; 208/48 R

[56] References Cited

U.S. PATENT DOCUMENTS

| | | | |
|---|---|---|---|
| 3,485,881 | 12/1969 | Zuech | 260/666 |
| 3,527,839 | 9/1970 | Glockner et al. | 260/683.15 |
| 3,631,121 | 5/1969 | Hutson, Jr. et al. | 260/683.15 |
| 3,636,128 | 1/1972 | Dunn et al. | 260/683.15 |
| 3,647,915 | 3/1972 | Bemer et al. | 260/683.15 |
| 3,655,810 | 4/1972 | Chauvin et al. | 260/683.15 |
| 3,771,966 | 11/1973 | Hutson, Jr. | 260/683.15 |
| 3,969,429 | 7/1976 | Belov et al. | 260/683.15 |
| 4,225,743 | 9/1980 | Heshiyama et al. | 585/512 |
| 4,242,531 | 12/1980 | Carter et al. | 260/683.15 |
| 4,283,305 | 8/1981 | Chauvin et al. | 585/512 |
| 4,309,387 | 1/1982 | Carter et al. | 260/683.15 |
| 4,320,243 | 3/1982 | Chauvin et al. | 585/521 |

Primary Examiner—D. E. Gantz
Assistant Examiner—Cynthia A. Prezlock
Attorney, Agent, or Firm—K. K. Brandes

[57] ABSTRACT

A method of pre-conditioning the walls of an olefin dimerization reactor and starting a dimerization process comprises sequential steps of introducing a first soluble homogeneous catalyst component comprising, e.g. a complex of a divalent metal selected from the group consisting of nickel, cobalt and iron, and a second soluble homogeneous catalyst component comprising, e.g. an organoaluminum compound, at rates such that the molar catalyst feed ratio of said aluminum to said divalent metal is maintained at a first value during the pre-conditioning and startup period and at a second, higher, value during the operating period.

31 Claims, 3 Drawing Figures

L = n-TRIBUTYLPHOSPHINE
EtAlCl$_2$ = ETHYLALUMINUMDICHLORIDE

SURFACE CONDITIONING IN OLEFIN DIMERIZATION REACTORS

BACKGROUND OF THE INVENTION

This invention relates to the dimerization of olefins in a reactor system. In one respect this invention relates to an improved method for the preconditioning, startup and operation of a reactor for the dimerization of olefins.

The dimerization of olefins is a well-known process in the art; see, e.g., Hutson and Carter, U.S. Pat. No. 3,631,121 (1971) and Zuech, U.S. Pat. No. 3,485,881 (1969). Olefin dimerization processes are applicable to olefins in general, however, dimerization is an especially attractive method for producing butylenes from ethylene for subsequent use in alkylation, dehydrogenation to butadiene and other chemical processes.

Zuech discloses in U.S. Pat. No. 3,485,881 that in dimerization reactions catalyzed by a first catalyst component containing nickel and a second catalyst component containing aluminum, the catalyst components are generally combined in proportions in the range from about 0.5 to about 20 moles of aluminum in the second component per mole of nickel in the first component. It was found desirable to use the upper portion of this range when desirable to scavenge catalyst poisons from the system. However, in order to minimize fouling of the interior reactor surface with polymer, it is now generally preferred that the aluminum/nickel molar feed ratio be relatively low, e.g., in the range of about 2.1:1 to about 7:1, as disclosed in my U.S. Pat. No. 4,242,531. Further, with the use of such relatively low catalyst aluminum/nickel ratios, the deposits that do form in the reactor and heat exchangers can be readily removed by washing with a 10 weight percent acetic acid solution.

Problems arise in dimerization processes in that the process suffers from low selectivity to the dimer, with much of the feed being converted to trimers and product heavies. It is known that selectivity can be improved by using shorter reactor residence time, but the disadvantages of this approach are low ethylene conversion and low catalyst productivity. Other problems arise when the feed stream is low in olefin concentration, e.g., only a small amount of ethylene with the remainder of the feed stream being gases such as hydrogen, methane, ethane, etc.

Accordingly, it is an object of this invention to provide an improved and more economical process for olefin dimerization.

Another object of this invention is to provide an olefin dimerization process with improved olefinic dimer selectivity and yield.

Another object of this invention is to provide an improved method for pre-conditioning and starting up a reactor for the dimerization of olefins, such that improved olefinic dimer selectivity and yield are obtained.

Other aspects, objects and advantages will be apparent from a study of this disclosure, the drawings and the appended claims.

SUMMARY OF THE INVENTION

In accordance with the invention, a process startup method for cleaned reactors has been devised which overcomes the deficiencies of prior art olefin dimerization processes such as low olefinic yield and low selectivity of the olefin to the olefinic dimer. The present invention is concerned with variations in reactor preconditioning and the process startup procedures to enable one to improve the olefin selectivity and/or yield in a dimerization process. It has been discovered that in a reactor system using a homogeneous catalyst having at least two components such as a metal alkyl and a transition metal complex for the dimerization of olefins, e.g., an aluminum alkyl and a nickel complex, the startup procedure can be modified by maintaining the molar feed ratio of two of the catalyst components during their initial introduction and the initial period of olefin introduction, below a first value which is less than a second value used for the subsequent dimerization operations, with the result that olefin selectivity and yield are improved. The reactor system is operated with the molar catalyst feed ratio of a second catalyst component to a first catalyst component being below said first value for a period of time which is sufficient to pre-condition the reactor system interior surface by contact with said first catalyst component. The invention is a conditioning process for a dimerization reactor. The clean, new, and/or cleaned reactor is treated as described prior to any significant dimerization operations taking place. In other words, the reactor interior surface (which is clean, new and/or after cleaning) is not exposed to any significant excursions of the molar catalyst feed ratio to excessive values above said first value prior to commencement of the dimerization operation phase. The invention is applicable to olefin dimerization processes in reactor systems using catalysts having at least a first soluble homogeneous catalyst component comprising a transition metal complex, e.g. a complex of a divalent metal selected from the group consisting of nickel, cobalt and iron, and at least a second soluble homogeneous catalyst component comprising an organometallic compound wherein the metal is selected from the group consisting of the metals of groups IA, II and IIIA of the Periodic Table, e.g. a metal alkyl such as an organoaluminum compound. Furthermore, the reactor can be operated longer before polymer fouling of reactor walls requires shutdown and cleaning.

DETAILED DESCRIPTION OF THE INVENTION

Figure 1:
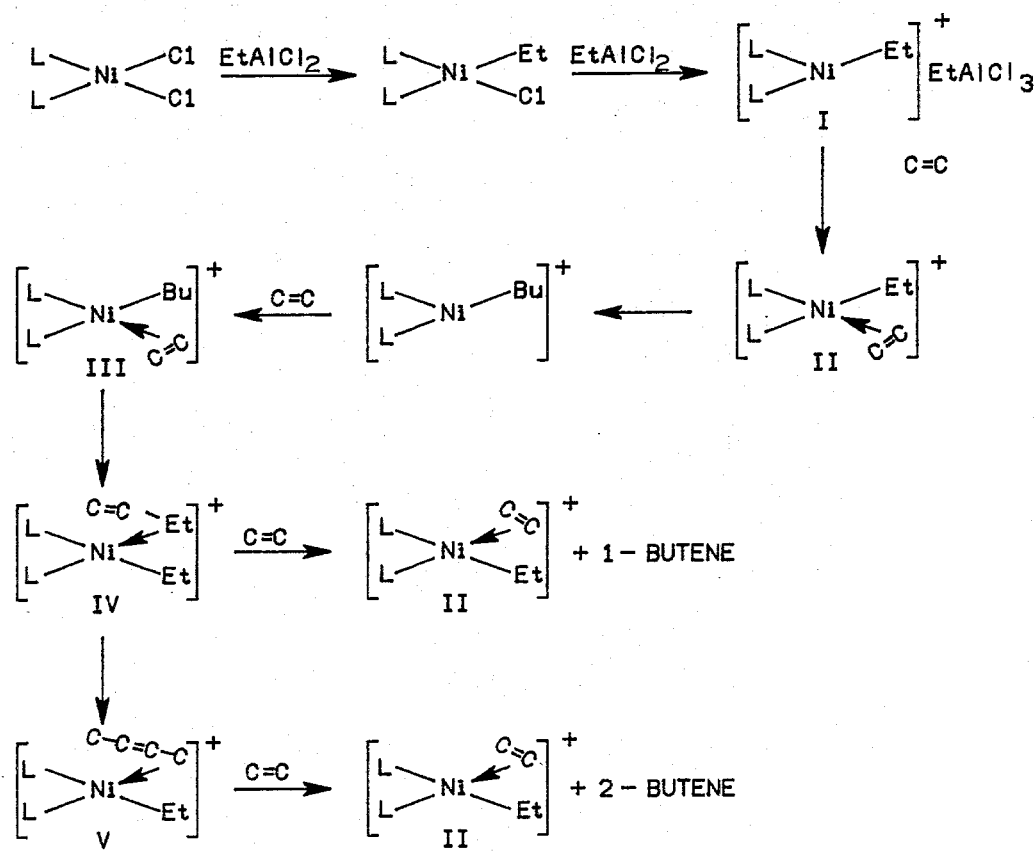
FIG. 1 describes a proposed mechanism of the dimerization reaction of ethylene in the presence of an ethylaluminum dichloride-nickel complex catalyst.

The dimerization of the olefinic feed can take place in any suitable reactor system, e.g. a loop reactor or stirred-tank reactor. The loop reactor is well known in the art, e.g., with or without the flash embodiments shown in my U.S. Pat. No. 4,242,531 (1980). The invention can be practiced with various appropriate homogeneous dimerization catalysts, as described herein. The catalysts presently preferred employed for ethylene dimerization, however, are generally those of any hydrocarbon-soluble nickel compound mixed with an alkyl aluminum halide, e.g., tri-n-butylphosphine nickel dichloride or bis(tri-n-butyl-phosphine)dichloronickel mixed with ethylaluminum dichloride.

Suitable process conditions of temperature and pressure can vary greatly for this invention and can be easily determined by one skilled in the art. Broadly, suitable temperatures can be in the range of from about 45 F. to about 150 F., preferably in the range from about 65 F. to about 125 F., and more preferably in the range from about 80 F. to about 100 F.

The invention method can be applied to the dimerization of hydrocarbon compounds having at least one terminal olefinic double bond, i.e. any suitable α-olefin (monoolefin or diene) linear or non-hindered branched, of up to twenty carbon atoms, with the invention method especially applicable to the selective dimerization of $C_2$ to $C_{10}$ α-olefins, such as ethylene, propylene, butenes, butadiene, decenes, etc., and most preferably, to α-olefins having 2 to about 6 carbon atoms. By "non-hindered" it is meant that the branches are not large enough or close enough to the reactive double bond to sterically hinder the dimerization reaction. Branches should not be closer than carbon atom number three, or one carbon from the double bond. Internal double bonds can be present, but generally do not affect the dimerization reaction. α-Olefins with a single terminal double bond are preferred, as α, ω-dienes (which have two terminal double bonds) tend to oligomerize rather than merely dimerizing. Ethylene is a preferred olefin reactant, however, as ethylene dimerization is an attractive method for producing butylenes from ethylene for subsequent use in alkylation, dehydrogenation to butadiene and other chemical processes. Mixtures of such olefins can be used as reactants, although the resulting dimer and codimer products will tend to be varied rather than uniform.

Although the invention is discussed herein with reference to ethylene as the olefin reactant to be dimerized, it is emphasized that this should not limit the invention in any way. The invention is applicable to any suitable α-olefin that can be dimerized, but the discussion will be in terms of ethylene for convenience, as that is a preferred olefin reactant.

Similarly, the ratio of the homogeneous catalyst components will be discussed in terms of the aluminum/nickel ratio, since the presently preferred catalyst components for ethylene dimerization are aluminum alkyls and nickel complexes, but the concept and effects of varying the ratio of two components of a homogeneous catalyst having at least two components during startup and/or pre-conditioning of a dimerization reactor apply generally to various catalysts for dimerization of olefins and are within the scope of the method of this invention. Although the ratio of catalyst components can be determined by any suitable method, for continuous process reactors as described herein it is presently preferred to calculate the ratio of the molar flow rates of the catalyst components at the catalyst inlets. Either instantaneous values or time-weighted averages of these flow rates can be used to calculate the ratio of molar flow rates. The resulting ratio of molar flow rates is effectively dimensionless.

This invention resides in the discovery that, in an olefin dimerization process, improved dimer selectivity and yield are obtained by initially utilizing in a clean reactor at least a first value of an Al/Ni mol ratio in a lower range than the normal operating range, (e.g., in the range of about 0.2 to less than about 2.0 for an ethylene dimerization process using an aluminum alkyl-nickel complex catalyst) for a pre-conditioning and startup period, and then raising the ratio to a second, higher, value, in the desired operating range for the normal operating period. For instance, in a preferred embodiment, by introducing the nickel complex or equivalent catalyst component first, the Al/Ni ratio value will initially be zero; then introduction of the aluminum component will increase this value. By contacting the reactor surface with the nickel component first, then the aluminum component, the resulting catalyst enables the selectivity and yield of ethylene to dimer to be increased. The nickel component should preferably be allowed to flow for a sufficient time (given the flow rate) to provide substantial contact of the nickel component with at least a portion of the interior surface of the reactor before the aluminum component flow begins or before there is substantial contact of the aluminum component with the reactor interior. Once the nickel component has contacted the reactor surfaces, the flow of the aluminum component can be initiated or increased, preferably at a rate which keeps the Al/Ni mol ratio in the desired low range during most of a pre-conditioning/startup period. The flow rate of the aluminum component, relative to the flow rate of the nickel component, can be gradually increased so that the desired Al/Ni ratio for normal dimerization operations is attained at or near the end of the startup period, or the aluminum component flow rate can be increased by a step change at the end of the startup period. Alternatively or additionally, once the aluminum component flow has reached a desired value, the flow of the nickel component can be decreased to further increase the value of the Al/Ni mol ratio during dimerization operations.

In general, the pre-conditioning and startup periods combined will total about 0.1 to about 25 hours, and preferably will total about 1 to about 18 hours or more preferably about 8 to about 12 hours. The second or normal operating period can extend for as long as production is desired, providing heat transfer is not excessively impaired by fouling of the reactor surfaces with polymer, e.g. the heat transfer coefficient is not reduced by more than 50 percent. Utilizing the method of the instant invention, a reactor system can be operated for at least up to about 2,000 hours, before such fouling requires a shut-down for cleaning. In general the second operating period will be in the range of about 300 to about 3000 hours, and preferably in the range of about 1000 to about 1500 hours.

PRIOR METHOD OF CLEANED REACTOR START UP

A conventional procedure to bring an ethylene dimerization reactor on stream is as follows:
(1) Fill the system with a solvent (non-olefinic, paraffin type hydrocarbon solvent, i.e., pentane, hexane, etc.).
(2) Start the circulation pump and circulate the solvent through the reactor system.
(3) Start injecting the aluminum catalyst component, e.g., ethylaluminum dichloride, to scavenge catalyst poisons in the solvent and reactor system.
(4) Start nickel catalyst complex addition.
(5) Begin ethylene flow to reactor.
(6) Adjust the catalyst rates and ethylene feed to give the desired product rate.

However, if this procedure is followed, the reacting system will start out with a very high aluminum to nickel ratio during the initial phases of the operation (first 24 hours of operation). This appears to produce a film on the interior surface of the reactor which has an adverse effect during the entire cycle between reactor cleaning operations. The net result is that the system operates at relatively low dimer selectivities and high heavies selectivities. Also, reactor operators typically realize that the aluminum alkyl is a scavenger for catalyst poisons. In an effort to get a cleaned reactor system up to specified rates in the shortest possible time period, there is a natural tendency to run at a higher than normal aluminum to nickel ratio during the startup period in an effort to remove such poisons, which aggravates this low dimer selectivity problem; see, e.g., U.S. Pat. No. 3,485,881, column 3, lines 60-65.

NOVEL METHOD OF CLEANED REACTOR PRECONDITIONING AND STARTUP

However, in accordance with the invention, if an alternate startup procedure is used, wherein the aluminum to nickel ratio is not allowed to reach high levels during the preconditioning/startup period, then a surface film formed at least partially from the catalyst components and/or their reaction products is apparently produced which favors high dimer selectivities and yield. An example of such a procedure is outlined as follows:

(1) Fill the system with a suitable cleaning solvent.
(2) Circulate the solvent for 20 to 30 minutes.
(3) Dump the cleaning solvent and charge a fresh batch of reaction solvent to the reactor.
(4) Start nickel catalyst addition at a catalyst feed rate sufficient for the anticipated initial flow of ethylene into the reactor.
(5) Start aluminum catalyst addition at a rate to give a controlled low Al/Ni ratio.
(6) Start ethylene flow to the reactor.
(7) Adjust and control the catalyst and ethylene feed rates to give the desired product rate (i.e., total flow rate of dimer and heavy products) while maintaining a stoichiometric excess of nickel catalyst (average Al/Ni catalyst ratio less than about 2:1) during the preconditioning/startup period (about 0.1 to about 25 hours). Temporary large excursions of the Al/Ni ratio above this value should be avoided.
(8) Adjust the nickel catalyst complex and/or aluminum rate to obtain by the end of the precondition/startup period, an aluminum to nickel catalyst mol ratio of about 2:1 or higher. Said 2:1 ratio is defined as stoichiometric by the mechanism given in FIG. 1 and discussed below. The Al/Ni ratio is preferably kept above this stoichiometric ratio during the operating phase. Once the reactor has shifted to the dimerization operating phase, the reaction can be carried on for as long as desired, or until fouling of reactor surfaces requires a shutdown for cleaning, e.g. about 2,000 hours.

The above procedure assumes that every effort has been made to drain and blow-down any free water in the reactor left from the cleaning operation before charging the solvent in Step 1, since water is a catalyst poison. The circulation and dumping of the first charge of solvent is to remove as much of the water from the system as is possible. In practice, Steps 1 through 3 may have to be repeated to achieve the required reduction in moisture in the system. This all depends on the physical configuration of the reactor unit and how completely the system can be blown-down to remove free water. The cleaning solvent and reaction solvent can be the same or different.

An advantage of the procedure of this invention is that the surface film produced in the reactor apparently promotes high dimer selectivity. Also, if the dimer product and/or heavy by-product from the reaction is used as the initial reactor charge in the procedure, a variety of catalyst poisons can be avoided. Since this by-product stream was produced in the reactor, it would be free from many of the poisons normally found in hydrocarbon solvents, with the exception of water (catalyst short stop). For example, a heavy by-product stream can be a kettle product from the separation section that typically follows the reactor, and with proper handling it can be obtained dry, e.g. water free. However, such heavy by-products should not be used as the solvent in the first (prior art) procedure outlined. This material is olefinic, and direct contact with free aluminum alkyl results in extremely fast fouling of the reactor surface by polymer. In the second (invention) procedure, the reactor surface is preconditioned in such a manner as to improve the overall dimerization reaction, e.g., promote the formation of desired dimer product. When nickel catalyst is added first, then butene product or heavy by-products can be used during both the initial period and operating period. The procedure of this invention permits the use of a heavy by-product as a solvent for initial charging of the reactor system in place of e.g. pentane.

CATALYST SYSTEMS

This invention is generally applicable to homogeneous catalysis processes for the dimerization of olefins using a hydrocarbon-soluble catalyst system having at least two components. The first catalyst component can be a transition metal complex, preferably containing a divalent metal selected from Group VIII of the Periodic Table, such as nickel, cobalt or iron. The second catalyst component can be an organometallic compound wherein the metal is selected from the group consisting of the metals of groups IA, II and IIIA of the Periodic Table, with lithium, magnesium, zinc and aluminum being preferred. Presently most preferred are organoaluminum compounds such as hydrocarbyl aluminum and hydrocarbyl aluminum halides.

The first catalyst component can be a hydrocarbon-soluble complex of nickel, cobalt or iron, preferably a substantially non-crystalline compound with an extensive $\pi$-electron system. Although the nickel complexes discussed herein are preferred because of availability and proven effectiveness, the equivalent complexes of cobalt and iron can also be used. The complexes useful in this invention include, but are not limited to, nitrosyl nickel complexes, N,N-dihydrocarbyldithiocarbamate nickel complexes, [bis]pyridine (or bipyridine) carboxylate nickel complexes, thiobisphenol nickel complexes, thiobisphenol nickel amine complexes, amine-N-oxide nickel complexes, and nickel complexes having the formula $L_2NiNOX$; where X can be any anion such as a halide, pseudohalide, alkoxide or the like such as $Cl^-$, $Br^-$, $SCN^-$, $NC^-$, $ONC^-$, and $CH_3O^-$, where L is either $R_3Q$ or $R_3QO$, where R is a hydrocarbyl group having from 1 to about 20 carbon atoms and Q is phosphorus, arsenic or antimony. Specific examples of these and other suitable types of nickel complexes and their preparations are given by Dunn in U.S. Pat. Nos.

3,558,738 (1971) and 3,636,128 (1972) and by Zuech in U.S. Pat. No. 3,485,881 (1969).

The second catalyst component can be, but is not limited to, an organometallic compound having the formula $R_xMX_y$, wherein R is a hydrocarbyl radical having from 1 to about 20 carbon atoms, X is a halide ion, M is a metal selected from group IA, II and IIIA of the Periodic Table (preferably lithium, magnesium, zinc or aluminum), x is an integer from 1 to 3, y is 0, 1 or 2, and x+y=the valence of M, e.g. 3 in the case of aluminum. The organoaluminum compounds are presently preferred. Of the organoaluminum compounds, alkyl aluminum halides and aluminum alkyls are presently preferred; specific examples are given by Dunn in U.S. Pat. No. 3,636,128 (1972).

The preferred catalyst used in the present examples was a homogeneous organometallic complex consisting of ethylaluminum dichloride and bis(tri-n-butylphosphine)nickel dichloride. Each catalyst component was prepared in dry normal pentane to facilitate handling and metering into the reactor. The catalyst solvent can be selected from any number of suitable hydrocarbons having in the range from 4 to about 13 carbon atoms, provided they are clean and dry. Olefinic solvents should be avoided for preparation or dispensing of the organoaluminum component, but the heavy by-products of the dimerization reaction having up to about six carbon atoms can be used for the preparation of the divalent metal complexes and for dispensing them, provided said by-products are clean and dry.

Catalyst components generally preferred for the dimerization of ethylene are alkyl aluminum halides or aluminum alkyls in combination with any hydrocarbon-soluble nickel compound.

PROPOSED MECHANISM OF THE CATALYZED DIMERIZATION REACTION

A proposed mechanism for generation of the active catalyst and the formation of ethylene dimer is shown in FIG. 1. The purpose of FIG. 1 is to show that two mols of aluminum compound are required per mol of nickel complex to activate the dimerization of ethylene to butenes. A detailed explanation of the mechanism is as follows: ethylaluminum dichloride reacts with the nickel complex to generate the cationic species I, which then coordinates with ethylene to give II. This undergoes an insertion reaction, followed by an ethylene coordination to produce the butyl-ethylene complex III. By a simple hydrogen transfer, III is converted to the ethyl-butene complex IV, which in turn can undergo an ethylene displacement to regenerate II and 1-butene. This step, of course, could involve a simple dissociation of the butene. In view of the fact the resultant butene is primarily the 2-isomer, the 1-butene complex IV probably undergoes an isomerization to give the 2-butene complex V, which can then react by the steps described above for complex IV to regenerate II.

In an alternative scheme, the butyl group from III might also cleave to form a hydride complex of the Type $L_2NiH$ (C=C) which could then revert to I by insertion of the ethylene on the complex or by insertion of another molecule of ethylene to give II. Propylene and the other olefins should react by a similar scheme, with the influence of the ligands L affecting the direction of insertion.

Thus FIG. 1 also illustrates the basis for two mols of alkyl aluminum halide to 1 mol of Ni complex which is defined as "stoichiometric" for activation of a particular two-component dimerization catalyst system.

When the system is operating with a relative (stoichiometric) excess of nickel catalyst as preferred, part of the nickel catalyst complex adheres to the reactor wall. The aluminum alkyl halide coming into contact with the nickel complex on the wall activates the nickel complex present rather than forming an aluminum halide coating on the reactor wall. The activated nickel complex then performs in the usual manner by dimerizing ethylene at the wall as in the bulk fluid. The net result then is a higher overall butene selectivity and yield per pass by maintaining an activated 2/1 stoichiometric catalyst complex for dimerization and by blocking ethylene polymerization reactions at the reactor surfaces.

DESCRIPTION OF A TYPICAL PROCESS

Figure 2:
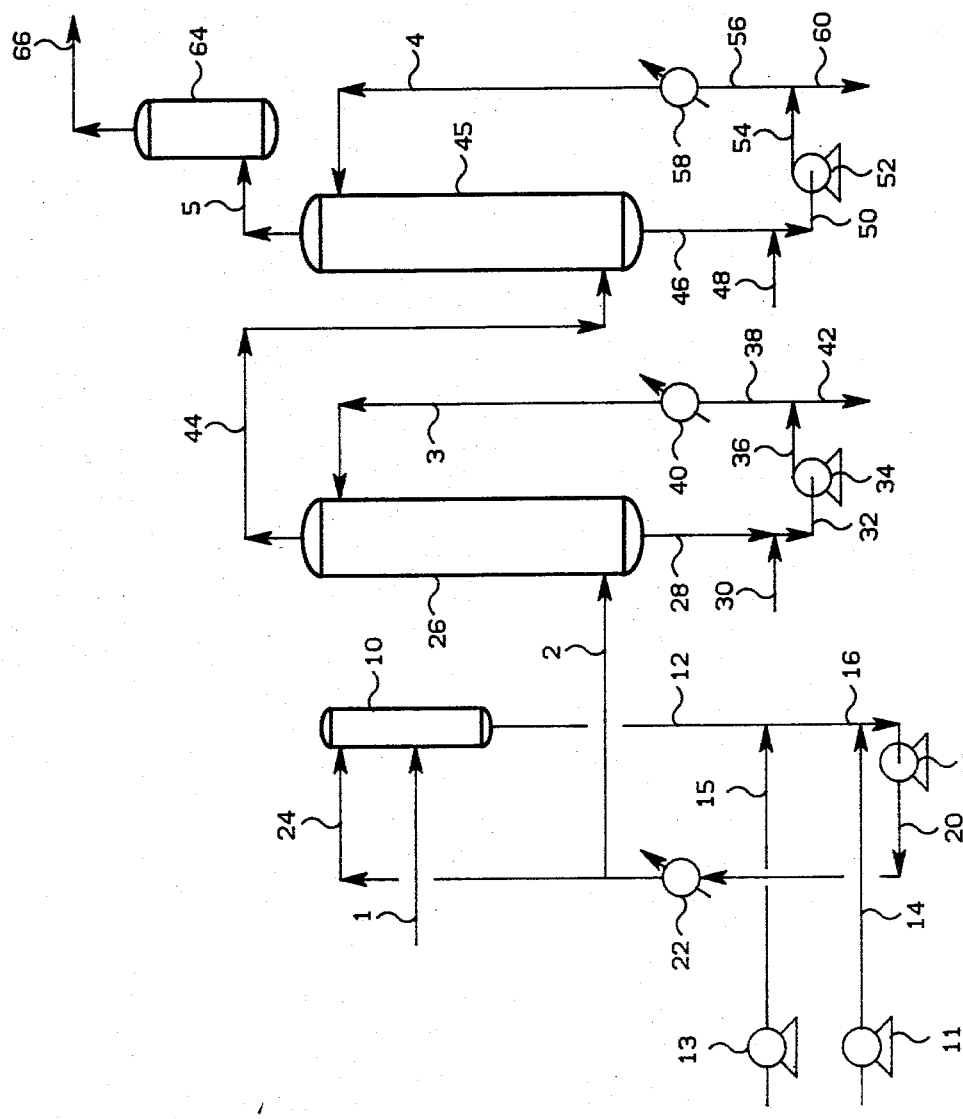
FIG. 2 is a schematic diagram of a dimerization reactor to which the invention is applied.

A dimerization process which catalytically converts ethylene to butylene in a typical phase reaction is illustrated in FIG. 2.

The dimerization process consists of three sections: a reaction step and two catalyst quench steps.

In the reactor section, ethylene is fed via conduit 1 to vessel 10 where ethylene mixes with diluent butenes, circulating via conduit 12. At least two catalyst components are introduced through pumps 11 and 13, flowing through conduits 14 and 15 and thence via conduit 16 to pump 18. Pumps 11 and 13 can be used, e.g., to start the flow of a first catalyst component before the other(s), and to control the molar feed ratio of the second catalyst component to the first catalyst component. In this invention, the catalyst average molar feed ratio is maintained below at a first value, during a first period of time, described as a pre-conditioning and startup phase, which is lower than the values customarily used during the second period of time, described as the dimerization operations phase. Pump discharge passes via conduit 20 through cooler 22 and back to vessel 10 in a circulating loop via conduit 24. Typical reaction conditions are 120 F., 200 psig, with average total residence time of the reactants in the circulating loop being about 30 minutes. Cooler 22 is used to remove the exothermic heat of ethylene dimerization.

If addition of the catalyst components is controlled during the pre-conditioning/startup phase at rates such that the aluminum to nickel mol ratio is in the range of about 0.2 to less than about 2.0, preferably in the range of about 0.5 to about 1.8, or more preferably in the range of about 0.7 to about 1.0, then the selectivity to dimer as well as conversion of ethylene and yield/pass of dimer will be significantly greater than when using Al/Ni mol ratios of, e.g., in the range of about 4 to 12 during this period. The value of the Al/Ni mol ratio is conveniently expressed as a time-weighted average of values calculated from measured flow rates during the preconditioning/startup phase. The flow rates can be controlled by suitable automatic control means or by manual adjustment to provide sufficient catalyst for the flow of ethylene and ratio values within the desired range. In one embodiment, the ratio is maintained at an essentially constant ratio, subject to minor statistical variations imposed by control means. Temporary variations in the ratio value above or below the desired average value are generally not harmful, provided their magnitude and duration are not excessive (i.e., sufficient to decrease dimer selectivity or conversion of feed), except that excessive increases in the ratio value are to be avoided in the early stages of the preconditioning phase, when it is important to have excess nickel present. In another embodiment, the flow of the nickel component can be initiated first, followed after a suitable time interval by the aluminum component so that the Al/Ni ratio is initially zero, then increases. The component flow rates are adjusted so that the ratio value gradually increases during the pre-conditioning/startup phase, attaining the desired average value for that phase and a suitable value for use during the operating phase by the end of said preconditioning/startup phase.

The objective of the pre-conditioning phase is to cover the interior reactor surface with a coating formed at least partially from the first and second catalyst components and/or reaction products thereof, said coating being of an amount and type effective to improve the selectivity and/or yield of dimer.

Once the pre-conditioning/startup phase is complete, the aluminum to nickel mol ratio should be increased (generally by decreasing the flow of nickel) to a suitable value for the operating phase. The average value of the aluminum to nickel mol ratio in the operations phase can be in the range of from about 0.5 to 20, preferably in the range of about 2 to about 7, and more preferably in the range of about 3 to about 5, in each case preferably representing a statistically significant increase (e.g. at least 10 percent) over the ratio utilized in the preconditioning/startup phase. Operating catalyst ratios in the low range, i.e. about 2 to about 7, are preferred to minimize fouling, as disclosed in my U.S. Pat. No. 4,242,531.

In this homogeneous liquid phase reaction, the reactor system internal surfaces appear to affect the selectivity, conversion, and yield quite markedly. Thus, reactor systems having a relatively high ratio of internal surface area to volume are preferred. Since this ratio in a loop reactor is inversely proportional to the loop tube diameter, a high surface area/volume ratio can be provided, e.g., by dividing at least one section of the flow through the loop into a series of relatively small diameter tubes, as e.g. a tube-shell heat exchanger or other suitable device which can be described as a multitube reactor. Depending upon the size of the reactor, a high surface area/volume ratio ($ft^{-1}$) can be in the range from about 5 to about 100. A high surface area/volume ratio improves heat transfer as well as providing more surface for the catalytic reaction. Generally, the instant invention and the reactions to which it applies are best carried out in a reactor system wherein the surface area/volume ratio is at least about 5/1 $ft^{-1}$. The invention can be practiced in reactors having interior surfaces of various materials having the desired heat transfer characteristics and smoothness, e.g. various steel alloys such as stainless or carbon steel, glass, ceramics, etc. Smoother surfaces will result in less frictional loss and less tendency for fouling by polymer.

High velocities are maintained in the reactor to minimize fouling and to minimize temperature rises across the reactor. A high recirculation rate is maintained in the reactor to achieve these velocities. Roughly, for every pound of product made from the reactor about 100 pounds of material are recirculated. This requires high pumping capacity to recirculate this material.

The catalyst for this reaction system is preferably a combination of bis(tri-n-butyl-phosphine)dichloronickel and ethylaluminum dichloride. These components are added at about 300 ppm quantities of total catalyst on the basis of the total bulk flowing fluid in the reactor system.

The material leaving the reactor is a liquid product containing unreacted ethylene, product butenes and catalyst and is sent to the catalyst quench section via conduit 2. The purpose of the catalyst quench section is to deactivate the catalyst and then separate most of the catalyst from the butene product. The nickel catalyst is killed when it comes in contact with acetic acid.

Reactor section effluent is passed via conduit 2 to quench vessel 26 where a recirculating acetic acid solution of about 2 weight percent contacts the butenes in an extractor vessel containing trays or the like to ensure good contact of the acid and butenes. Extractor bottoms are circulated via conduit 28 where said bottoms are contacted with make up acetic acid solution via conduit 30 and pass via 32 to pump 34 to be recirculated to quench vessel 26 via conduits 36 and 38 and cooler 40 via conduit 3. A small purge of deactivated nickel catalyst is removed via conduit 42. The butene stream leaving the top of the extractor via conduit 44 will contain a small quantity of acetic acid. These butenes are neutralized in extractor vessel 45 with dilute caustic soda solution entering via conduit 48. The neutralization mixture of butenes and aqueous caustic passes via conduits 46 and 50 to circulating pump 52. A stream of fresh caustic enters pump section 50 via conduit 48. Pump 52 recirculates butenes and caustic solution via lines 54 and 56 to cooler 58 and conduit 4 back to vessel 45. A small purge of spent caustic leaves the circulating loop via conduit 60. The butene stream exits extractor 45 via line 5 to sand filter vessel 64 where it exits via product line 66.

A calculated material balance relevant to FIG. 2 and typical of the process is illustrated by Table I as follows:

TABLE I

| Component | Material Balance* Stream Nos. | | | | |
|---|---|---|---|---|---|
| | 1 | 2 | 3 | 4 | 5 |
| Ethylene | 100.0 | 7.0 | 21.0 | 21.0 | 3.5 |
| Butenes | | 86.6 | 259.8 | 259.8 | 86.6 |
| Hexenes | | 6.4 | | 2.4 | 6.4 |
| Sodium Hydroxide | | | | 561.1 | |
| Acetic Acid | | | 561.1 | | |
| Water | | | 28056.1 | 8016.0 | |
| Total | 100.0 | 100.0 | 28898.0 | 8860.3 | 96.5 |

*(Component and total values are in thousands of Lbs/Hr.)

The invention is further illustrated by the following example, which should not be regarded as more limiting than the appended claims. Unless otherwise noted, all percentages and/or parts are by weight.

EXAMPLE I

Ethylene dimerization experiments were conducted on a pilot plant scale using a circulating loop reactor and a two-component catalyst of ethylaluminum dichloride and bis(tri-n-butylphosphine)dichloronickel.

A typical procedure essentially common to this experimental example was as follows: The pipe loop reactor system was first filled with solvent, typically n-pentane, and said solvent was circulated for about one-half hour, after which said solvent was dumped to disposal. A second charge of fresh solvent (n-pentane) was pumped into the reactor system, after which the flow of nickel catalyst component was begun, followed by aluminum catalyst component addition and finally by ethylene flow addition. Final adjustments were made to the nickel and aluminum catalyst and ethylene flow rates to establish the desired experimental parameters.

To illustrate the importance of the initial reactor pre-conditioning at low Al/Ni mol ratios, Table II presents selected data points from Runs 1, 2, 3, and 4. In control Runs 1 and 2, the system was charged with normal pentane, and ethylaluminum dichloride was circulated through the system to scavenge poisons from the system before the nickel complex catalyst component was introduced. The average Al/Ni catalyst ratios were calculated by a time-weighted average of hourly readings. In these runs, an effort was generally made to maintain a constant value for the Al/Ni mol ratio during the startup phase to the extent possible. The statistical tolerance limits calculated indicate the limits within which 95 percent of the ratio values would be expected to fall. Tolerance limits were calculated as $\pm t_{0.95} S\sqrt{n}$, where $t_{0.95}$ is a double-sided t-test, S is sample standard deviation and n is degrees of freedom (number of runs-1). Runs 1 and 2 were activated using a relatively high Al/Ni catalyst ratio during the preconditioning/startup phase while runs 3 and 4 were activated using low Al/Ni catalyst ratios during the preconditioning/startup phase and higher ratios during the operating phase. The average catalyst ratio values of Runs 1 and 2, 10.6 and 8.5, were higher than the operating ratios of 4.9 and 4.5, respectively. The values for the operating ratios in Tables II and III were time-weighted averages for 8-hour segments including a specific process time, i.e. a specific stage of the operating phase, as measured from the start of the preconditioning/startup phase. In invention Runs 3 and 4, the nickel was introduced first, giving low initial catalyst ratios, (2.3 and 0.8, respectively), with the operating ratios being higher (4.1 and 2.4, respectively). Better selectivities to butenes were obtained. The extrapolation of Run 4 data to match the conditions of the point from Run 3 (involving the greatest temperature correction), matched the selectivities of the data point from Run 3 with a deviation of less than one percentage point in selectivity. The extrapolation of Run 4 to the conditions of the data point from Run 1 showed an average increase of 36.3 percent in selectivity when compared to runs made at similar operating conditions. That is, the selectivity to butenes for low initial Al/Ni mol ratios was 36.3 percent higher than with high initial Al/Ni mol ratios. Similarly, the deviation for the data point from Run 2 was 25.8 percent in butenes selectivity. This clearly illustrates that how the reactor is started-up and put on-line can significantly affect the performance of the reactor many hours into the run. The selected data points were at process times of 114 to 516 hours into each run.

Figure 3:
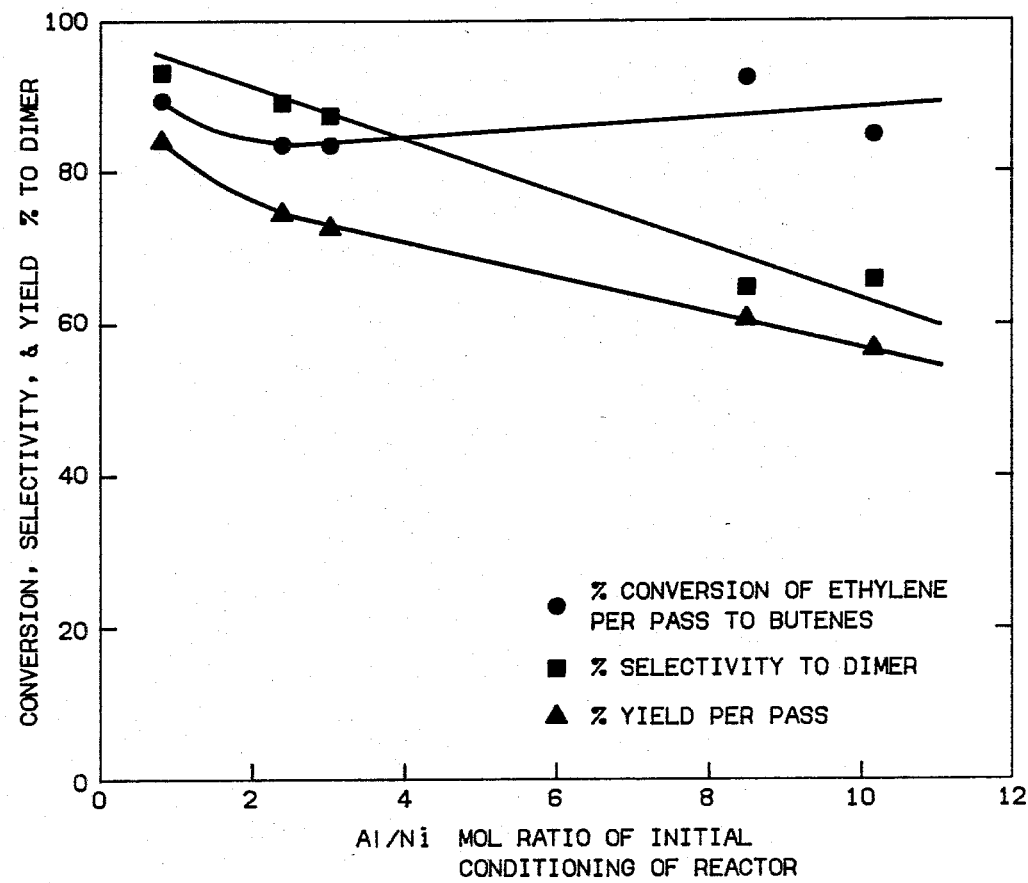
FIG. 3 illustrates the variations in conversion, yield and selectivity of an ethylene dimerization reaction with the catalyst aluminum/nickel ratio used in initial conditioning of the reactor.

Table III is an expansion of Table II to include the average reactor temperature, average reactor pressure, average operating catalyst ratio, average ethylene conversion, and average butenes yield, with an additional Run 5 and different process times for Runs 1–4. Run 5 was a transitional run in which the aluminum component was introduced first, resulting in an undesirable Al/Ni mol ratio of about 18/1 after the first hour. The flow of nickel component was immediately increased, thus reducing the average initial catalyst ratio to 3.0. Although the average operational catalyst ratio was lower at 1.5, Run 5 produced higher butenes selectivity and yield than Run 2. However, Runs 3 and 4, in which the catalyst ratios were low during the pre-conditioning/startup phase and increased to an operational value in the preferred range, gave still higher selectivities and yields. Data from Table III is illustrated graphically in FIG. 3. By definition yield per pass is equal to conversion per pass times selectivity to butene dimer. FIG. 3 clearly shows that with low Al/Ni mol ratios during initial conditioning and startup of the reactor, the yield per pass to butenes increases significantly, compared to the results with higher Al/Ni mol ratios during the initial conditioning of the reactor.

The loop reactor used was a double-pipe heat exchanger made in four series-connected sections of about 12 feet each. Two of the sections were constructed of 1-inch stainless steel tubing in 1½-inch schedule 80 pipe and two sections of 1-inch carbon steel tubing in 1½-inch schedule 80 pipe. All four sections were connected in series. The walls of the tubing were on the order of 100 times smoother than carbon steel pipe used in a typical pilot plant. Smooth tubes give greatly reduced friction between flowing fluid and wall. This results in marked reduction in tube fouling. Although such smooth tubes are preferred to minimize friction and fouling and to thus improve heat transfer, they are not required for the practice of this invention. The inner surface area/volume ratio of the reactor was about 16.7 ft$^{-1}$, except in Run 4, where the ratio was about 29.7 ft$^{-1}$.

In spite of the different surface area/volume ratio of run 4 at 29.7 A/V compared with runs 1, 2, 5, and 3 at 16.7 A/V, said run 4 provides comparative data for the effect of pre-conditioning with a nickel compound preceding an organoaluminum compound, because the observed effect of the surface area/volume ratio in other experiments was secondary.

TABLE II

| Run No. | Average Initial Catalyst Ratio ± Tolerance[1] | Precond/ Start-up Phase Hours | Total Time on Stream hours | Process[2] Time hours | Oper.[3] Cat. Ratio | Avg. Reactor Temp. °F. | Avg. Reactor Press. PSIA | $C_2^=$ Conv. % | Selectivities $C_4^=$'s % | $C_n+$ % |
|---|---|---|---|---|---|---|---|---|---|---|
| 1 | 10.6 ± 3.3 | 23 | 494 | 114 | 4.9 | 99 | 320 | 98.8 | 50.6 | 49.4 |
| 2 | 8.5 ± 0.8 | 15 | 304 | 157 | 4.5 | 103 | 300 | 93.4 | 62.6 | 37.4 |
| 3 | 2.3 ± 0.2 | 10 | 497 | 382 | 4.1 | 112 | 300 | 84.6 | 88.9 | 11.1 |
| 4 | 0.8 ± 0.7 | 7 | 1115 | 219 | 2.4 | 72 | 300 | 76.3 | 96.7 | 3.3 |
| 4 | 0.8 ± 0.7 | 7 | 1115 | 516 | 2.4 | 81 | 309 | 80.6 | 96.6 | 3.4 |
| 4 | 0.8 ± 0.7 | 7 | 1115 | 211 | 2.4 | 93 | 300 | 80.4 | 96.5 | 3.5 |
| 4 | 0.8 ± 0.7 | 7 | 1115 | 243 | 3.2 | 76 | 300 | 91.6 | 94.6 | 6.4 |

[1]Statistical tolerance = ± $t_{0.95} S\sqrt{n}$
[2]Measured from start of preconditioning/start-up phase
[3]Averages for 8-hour segments at stated process time
[4]Catalyst ratio is ratio of molar flow rates, Al/Ni.

TABLE III

| Run No. | Average Initial Catalyst Ratio Al/Ni mols/mol | Total Process Time hrs. | Avg. Reactor Temp °F. | Avg. Reactor Press PSIA | Average Operating Catalyst Ratio Al/Ni mols/mol | Average C₂= Conversion % | Overall Av Select C₄= % | Overall Av Select C₆+ % | Av C₄= Yield % |
|---|---|---|---|---|---|---|---|---|---|
| 1 | 10.6 | 494 | 105 | 316 | 9.2 | 85.7 | 66.0 | 34.0 | 56.5 |
| 2 | 8.5 | 304 | 115 | 300 | 5.6 | 93.9 | 64.3 | 35.7 | 60.4 |
| 3 | 2.3 | 497 | 87 | 300 | 5.1 | 83.9 | 89.4 | 10.6 | 75.0 |
| 5* | 3.0 | 55 | 110 | 300 | 1.5 | 83.6 | 87.7 | 12.3 | 73.3 |
| 4 | 0.8 | 1115 | 80 | 300 | 2.7 | 82.4 | 95.8 | 4.2 | 78.9 |
|  |  |  | 85 | 159 | 3.3 | 94.2 | 93.5 | 6.5 | 88.1 |
|  |  |  | 85 | 74 | 2.1 | 99.5 | 82.0 | 18.0 | 81.6 |
| Time-Weighted Av. for Run 4 |  |  | 84 | 194 | 3.0 | 91.1 | 94.2 | 5.8 | 85.8 |

*Total time on stream 55 hours, average catalyst ratio tolerance ± 1.4.
1. Averages for 8-hour segments at stated process time
2. See note 2, Table II.
4. See note 4, Table II.

These data demonstrate the surprising result that in this homogeneous catalyst system for olefin dimerization, the selectivity and yield are significantly affected by the initial conditioning of the reactor's surfaces. A coating or film appears to form on the reactor surfaces to markedly influence the dimerization reactions in the presence of said homogeneous catalyst system. By comparing the results of Run 4 with those of Runs 1, 2, 3 and 5 of Table III, one can conclude that the use of low Al/Ni mol ratios, i.e. less than about 2/1, during this initial conditioning phase, then increasing the ratio significantly, preferably to greater than 2/1, during the dimerization operation phase improves dimer selectivity and yield during the dimerization operations phase.

Various modifications and alterations of this invention will become apparent to those skilled in the art without departing from the scope and spirit of this invention. The foregoing discussion and examples merely illustrate preferred embodiments of this invention and do not unduly limit the same.

I claim:

1. A method for dimerizing at least one α-olefin in a reactor comprising the steps of:
    (a) contacting the surface of said reactor with a homogeneous catalyst selective to dimerization, comprising at least one hydrocarbon-soluble nickel compound as first catalyst component, and at least one organoaluminum compound selected from the group consisting of hydrocarbyl aluminum halides and hydrocarbyl aluminum as second catalyst component, wherein the feed rates of said first and second catalyst components are adjusted so as to give a molar ratio of aluminum in said second catalyst component to nickel in said first catalyst component (Al/Ni mol ratio) being below a first value;
    (b) introducing at least one α-olefin having from 2 to 20 carbon atoms into said reactor;
    (c) operating said reactor under such conditions as will result in the dimerization of the α-olefin, with the Al/Ni mol ratio of the catalyst being below said first value, for a first period of time ranging from about 0.1 to about 25 hours so as to pre-condition the interior surface of said reactor; and
    (d) thereafter operating said reactor for a second period of time with the feed rates of said first and second catalyst components adjusted so as to give an Al/Ni mol ratio of the catalyst being at a second value which is higher than said first value.

2. A method in accordance with claim 1 wherein said first catalyst component is selected from the group consisting of hydrocarbon-soluble nickel complexes and said second catalyst component is selected from the group consisting of alkyl aluminum halides, wherein the alkyl group has from 1 to 20 carbon atoms.

3. A method in accordance with claim 2 wherein said first catalyst component is bis(tri-n-butyl-phosphine)dichloronickel and said second catalyst component is ethylaluminum dichloride.

4. A method in accordance with claim 2, wherein the average Al/Ni mol ratio of the catalyst during said second period of time is at least about 10 percent greater than the average Al/Ni mol ratio of the catalyst during said first period of time.

5. A method in accordance with claim 2 wherein said first value of said Al/Ni mol ratio is about 2.0.

6. A method in accordance with claim 2 wherein during most of said first period of time the Al/Ni mol ratio is maintained in the range of from about 0.2 to a higher value being less than about 2.0.

7. A method in accordance with claim 2 wherein during most of said first period of time the Al/Ni mol ratio is maintained in the range of from about 0.5 to about 1.8.

8. A method in accordance with claim 2 wherein during most of said first period of time the Al/Ni mol ratio is maintained in the range of from about 0.7 to about 1.0.

9. A method in accordance with claim 2 wherein said second value of the Al/Ni mol ratio during said second period of time is in the range of about 2 to about 7.

10. A method in accordance with claim 2 wherein said second value of the Al/Ni mol ratio during said second period of time is in the range of from about 3 to about 5.

11. A method in accordance with claim 1 wherein a portion of said first catalyst component is introduced to said reactor first, followed by said second catalyst component, and the feed rates thereof are varied such that the Al/Ni mol ratio of the catalyst increases gradually from zero to close to said first value at the end of said first period of time.

12. A method in accordance with claim 11, wherein said first catalyst component contacts at least a portion of said interior surface of said reactor before said surface is contacted by said second catalyst component.

13. A method in accordance with claim 1 wherein said α-olefin contains from 2 to 10 carbon atoms.

14. A method in accordance with claim 1 wherein said α-olefin contains from 2 to 6 carbon atoms.

15. A method in accordance with claim 1 wherein said α-olefin is ethylene.

16. A method in accordance with claim 1 wherein said reactor comprises a continuous circulating loop reactor or a continuous stirred-tank reactor.

17. A method in accordance with claim 16 wherein the ratio of the interior of said reactor surface to the volume ratio of said reactor system is at least about 5/1 $ft^{-1}$.

18. A method in accordance with claim 1 wherein the thus pre-conditioned surface of said reactor is covered with a coating formed at least partially from said first and second catalyst components and/or reaction products thereof.

19. A method in accordance with claim 1 wherein the solvent used during said second period of time comprises dimer reaction products of said α-olefin.

20. A method in accordance with claim 1 wherein said reactor is charged with a suitable solvent comprising heavy by-products of the dimerization of said at least one α-olefin.

21. A method in accordance with claim 1 wherein the operating temperature during said first and second periods of time is in the range of from about 45° F. to about 150° F.

22. A method in accordance with claim 1 wherein the operating temperature during said first and second periods of time is in the range of from about 65° F. to about 125° F.

23. A method for dimerizing at least one α-olefin in an olefin dimerization circulating loop reactor, comprising the steps of:
  (a) contacting the surface of said reactor with a first homogeneous catalyst component comprising a complex of divalent nickel, and a second soluble homogeneous catalyst component comprising an alkyl aluminum halide, wherein the alkyl group has from 1 to 10 carbon atoms;
  (b) introducing at least one α-olefin having from 2 to 20 carbon atoms into said reactor;
  (c) operating said reactor for a first period of time ranging from about 0.1 to about 25 hours, under conditions as will result in the dimerization of said α-olefin, while controlling the feed rates of said catalyst components such that the average molar ratio of the aluminum in said alkyl aluminum halide to said divalent nickel in said complex (Al/Ni mol ratio) is maintained for the first period of time in a first range of ratio values which is effective to improve the selectivity and/or yield of dimer during a second period of time;
  (d) subsequently adjusting said Al/Ni mol ratio of the catalyst to a second value, higher than the average ratio value during said first period of time, for dimerization operations during a second period of time; and
  (e) operating said reactor to produce dimer for said second period of time.

24. A method in accordance with claim 23 wherein said average Al/Ni mol ratio during said first period of time and the duration of said first period are effective to coat the interior surface of said reactor with an amount and type of coating effective to improve said selectivity and/or yield.

25. A method for dimerizing at least one α-olefin in a cleaned reactor comprising the steps of:
  (a) contacting the surface of said reactor with a homogeneous catalyst selective to dimerization and having a first catalyst component comprising a complex of divalent nickel and a second catalyst component comprising an alkyl aluminum halide, wherein the alkyl group has from 2 to 20 carbon atoms;
  (b) introducing at least one α-olefin having from 2 to 20 carbon atoms into said reactor under such conditions as will result in the dimerization of said α-olefin;
  (c) operating said reactor with the feed rates of said first and second catalyst components controlled so that the average value of the Al/Ni mol ratio of said second catalyst component to said first catalyst component is below a first value for a first period of time sufficient to pre-condition the interior surface of said reactor by contact with said first catalyst component; and
  (d) thereafter operating said reactor for a second period of time with said molar catalyst feed rates controlled to maintain an average value of said Al/Ni mol ratio higher than the average value of said Al/Ni mol ratio during said first period of time.

26. A method in accordance with claim 25 wherein said average value of said Al/Ni mol ratio during said second period of time is at least about 10 percent higher than said first value.

27. A method in accordance with claim 25 wherein said first value is about 2.

28. A method in accordance with claim 3 wherein the α-olefin is ethylene and the first value of the Al/Ni mol ratio of the catalyst is about 2.0.

29. A method in accordance with claim 28 wherein the operating temperature during said first and second periods of time is in the range of about 65° F. to about 125° F.

30. A method in accordance with claim 29 wherein said first period of time ranges from about 1 to 18 hours.

31. A method for dimerizing at least one α-olefin in a reactor comprising the steps of:
  (a) contacting the surface of said reactor with a homogenous catalyst selective to dimerization, comprising at least one complex of a divalent metal selected from the group consisting of nickel, cobalt and iron as first catalyst component and at least one organoaluminum compound as second catalyst component, wherein the feed rates of said first and second catalyst components are adjusted so as to give a molar ratio of aluminum in said second catalyst component to the divalent metal in said first catalyst component being below a first value;
  (b) introducing at least one α-olefin having from 2 to 20 carbon atoms into said reactor;
  (c) operating said reactor under such conditions as will result in the dimerization of the α-olefin, with said molar ratio of aluminum to the divalent metal of the catalyst being below said first value, for a first period of time ranging from about 0.1 to about 25 hours so as to pre-condition the interior surface of said reactor; and
  (d) thereafter operating said reactor for a second period of time with the feed rates of said first and second catalyst components adjusted so as to give a molar ratio of aluminum to said divalent metal of the catalyst being at a second value which is higher than said first value.

* * * * *